United States Patent [19]

Kosaka

[11] Patent Number: 5,469,375
[45] Date of Patent: Nov. 21, 1995

[54] DEVICE FOR IDENTIFYING THE TYPE OF PARTICLE DETECTED BY A PARTICLE DETECTING DEVICE

[75] Inventor: Tokihiro Kosaka, Kakogawa, Japan

[73] Assignee: Toa Medical Electronics Co., Ltd., Kobe, Japan

[21] Appl. No.: 11,812

[22] Filed: Feb. 1, 1993

[30] Foreign Application Priority Data

Jan. 30, 1992 [JP] Japan ................................ 4-042319

[51] Int. Cl.$^6$ ............................ G06F 15/46; G06F 15/52
[52] U.S. Cl. .................... 364/555; 364/496; 364/413.08
[58] Field of Search ............................. 364/555, 413.07, 364/413.08, 496, 497, 498; 356/39, 40, 41, 42; 382/6

[56] References Cited

U.S. PATENT DOCUMENTS

| | | | |
|---|---|---|---|
| 3,870,872 | 3/1975 | Johnson | 364/413.08 X |
| 4,008,388 | 2/1977 | McLafferty et al. | 235/151.35 |
| 4,661,913 | 4/1987 | Wu et al. | 364/500 |
| 4,741,035 | 4/1988 | Bahl et al. | 381/43 |
| 5,040,112 | 8/1991 | Marshall et al. | 364/413.08 |
| 5,124,932 | 6/1992 | Lodder | 364/497 |

OTHER PUBLICATIONS

"Clinical Significance of New Coagulation and Fibrinolytic Markers in Ischemic Stroke Patients", by Noriko Ono et al., Stroke, vol. 22, No. 11, Nov. 1991, pp. 1369–1373.

Primary Examiner—Emanuel T. Voeltz
Assistant Examiner—M. Kemper
Attorney, Agent, or Firm—Banner & Allegretti, Ltd.

[57] ABSTRACT

A device for identifying the kind of each particle detected by a particle detecting device such as imaging flow cytometer from detection signals obtained by passing therethrough a specimen, such as blood, in which various kinds of particles (blood corpuscles) exist intermixedly. Distribution characteristics (mean value, distribution width, etc.) of specific physical values previously obtained on a known kind of reference particles are stored, the degree of similarity of the detected particle to the reference particles, that is, "probability of correctness of judgement at the time of judging the detected particle as of the same kind of the reference particles" is calculated, in accordance with a predetermined, rule from the particle detection signals representing the same physical values and the stored distribution characteristics of the reference particles, and the probabilities calculated on the respective physical values are synthesized to judge whether or not the detected particle is of the same kind as the reference particles.

6 Claims, 3 Drawing Sheets

DEVICE FOR IDENTIFYING THE TYPE OF PARTICLE DETECTED BY A PARTICLE DETECTING DEVICE

BACKGROUND OF THE INVENTION

This invention relates to a device for identifying the kind of each particle based upon detection signals obtained by passing a specimen such as blood, in which plural kinds of particles such as blood corpuscles exist intermixedly, through a particle detecting device such as a flow cytometer.

With a flow cytometer, it is possible to detect each blood corpuscle in the blood and count the number of blood corpuscles and, also, to obtain various detection signals corresponding to each blood corpuscle, which signals suggest the kind corpuscle, by applying predetermined preliminary treatment to the blood. The detection signals are quantitative representations of various physical quantities (hereinunder referred to as "characteristic or physical parameters") such as scattered light intensity, fluorescence intensity, light absorption, particle diameter, particle area and N/C ratio (the ratio of nucleus and cytoplasm, when the particle is formed thereof) which suggest the kind of corresponding particle. Some methods and devices for identifying the kind of blood by corpuscle by using such detection signals have been known already as disclosed in U.S. Pat. Nos. 3,883,247 and 4,596,035, for example. According to these prior art techniques, however, sub-populations or "clusters" formed of respective kinds of blood corpuscles are sought from a frequency distribution diagram or histogram, or a correlative distribution diagram of the detection signals of a substantial number of particles in order to know quantitative proportions thereof, and it is impossible to know the kind of each blood corpuscle which is passing through a detecting area of the flow cytometer in real time fashion. It should be exceedingly advantageous for speeding up quantitative analysis of particle mixtures such as blood, if the kind of each particle passing through the detecting area of the particle detecting device such as a flow cytometer could be identified in real time fashion. However, only the following prior art system has been proposed as enabling such a speedier analysis. This system is based upon the principle that the value of each physical parameter substantially falls within a specific range relating to the kind of particle.

As shown in FIG. 1, detection signals X1 and X2 representing a suitable two of the above physical parameters are selected and their upper limits X1max and X2max and lower limits X1min and X2min, which are experientially selected for a specific kind of particle, are stored in upper limit registers 10 and 12 and lower limit registers 14 and 16, respectively. The detection signals X1 and X2 are supplied respectively to a pair of comparators 18 and 20 and another pair of comparators 22 and 24 and compared with the contents of the upper and lower limit registers 10 and 14 and the upper and lower limit registers 12 and 16. The comparators 18 and 20 deliver "high" level signals to an AND gate 26 when the signal X1 is within the prescribed range and, similarly, the comparators 22 and 24 deliver "high" level signals to an AND gate 28 when the signal X2 is within the prescribed range. The outputs of both AND gates are supplied to an AND gate 30 and, therefore, the AND gate 30 delivers a "high" level output when both detection signals are within the prescribed ranges, respectively. When the output signal of the AND gate 30 is of "high" level, it is judged that the particle which provides these detection signals shall belong to the specific kind. Although, two kinds of physical parameters are used in FIG. 1 three or more kinds of physical parameters may be used, and the accuracy of judgement will rise with the number of kinds. As is obvious from FIG. 1, however, it is judged that the particle does not belong to the specific kind in this logic circuit, if even one of the outputs of the comparators 18, 20, . . . is of "low" level. Therefore, there is a substantial chance of judging "true" as "false". However, if the prescribed range is expanded for removing the above problem, the probability of judging "false" as "true" will rise to reduce the accuracy of judgement.

As described above, the prior art technique could not obtain accurate judgement without mistake and, moreover, it could not numerically indicate the degree of certainty, or the probability of correctness, of each judgement.

Accordingly, an object of this invention is to provide an improved particle judging device which can identify the kind of each particle caught by a particle detecting device at high accuracy in real time fashion and, also, numerically indicate the probability of correctness of the judgement.

SUMMARY OF THE INVENTION

The above object is achieved in accordance with this invention which provides a particle judging device comprising means for providing a detection signal representing at least one physical parameter of each particle, being detected means for storing distribution characteristics of the same physical parameter which were previously obtained on a specific kind of particles, data converting means for converting the detection signal based upon these distribution characteristics of the same physical parameter in accordance with a predetermined rule,in order to calculate the probability of each detected particle being a particle of the specific kind, and means for comparing the calculated probability with a predetermined reference value to judge whether the particle belongs to the specific kind or not.

In a preferred example, the stored distribution characteristics are a mean value and a distribution width, and the data converting means includes means for calculating the deviation of the detection signal from the mean value, means for normalizing the deviation based upon the distribution width and means for converting the normalized deviation in accordance with a predetermined function.

Now, these and other features and functions of this invention will be described in more detail below about a preferred embodiment thereof with reference to the accompanying drawings.

BRIEF DESCRIPTION OF THE DRAWINGS

In the drawings.

Throughout the drawings, same reference numerals are given to the same structural components.

DESCRIPTION OF THE PREFERRED EMBODIMENT

Figure 1:
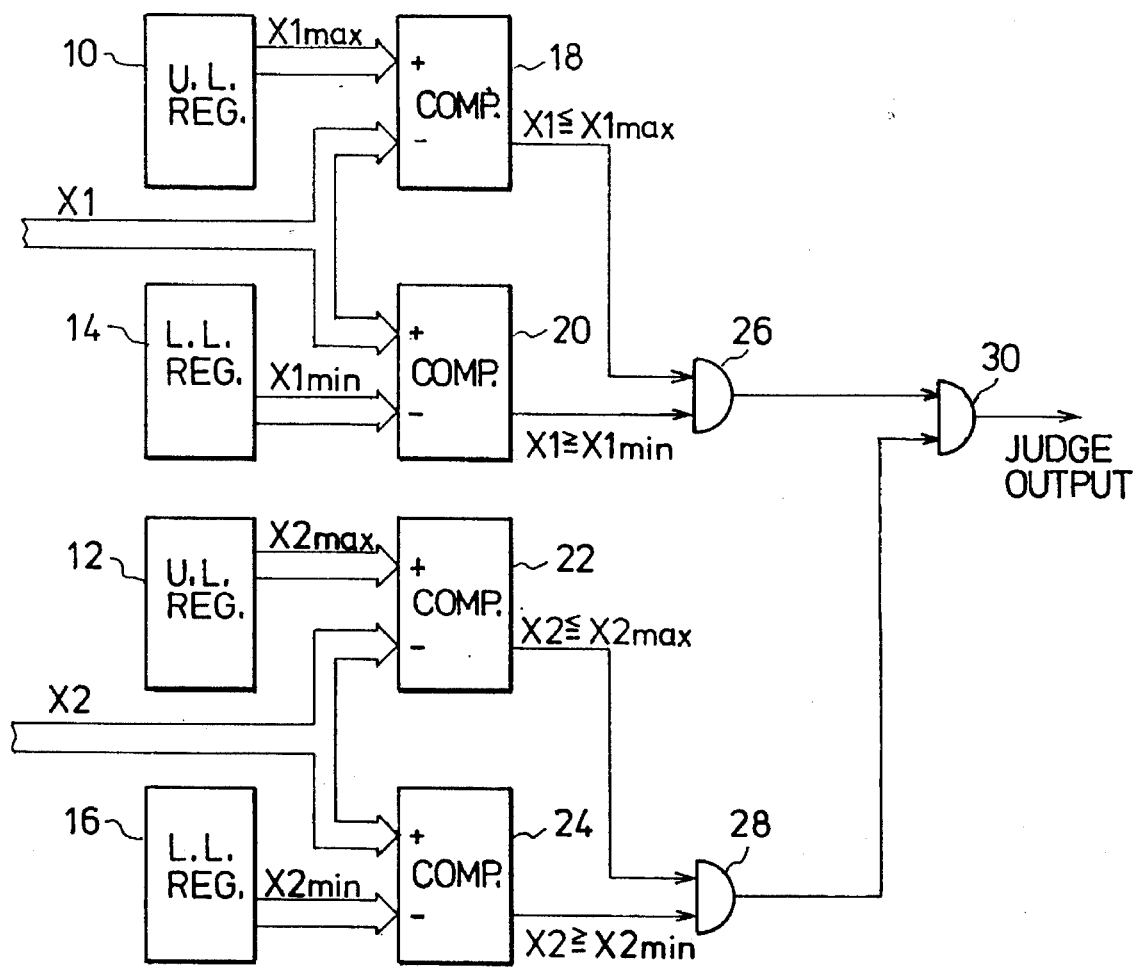
FIG. 1 is a block diagram showing a configuration of a particle judging device according to prior art, which is a start point of this invention.
Figure 2:
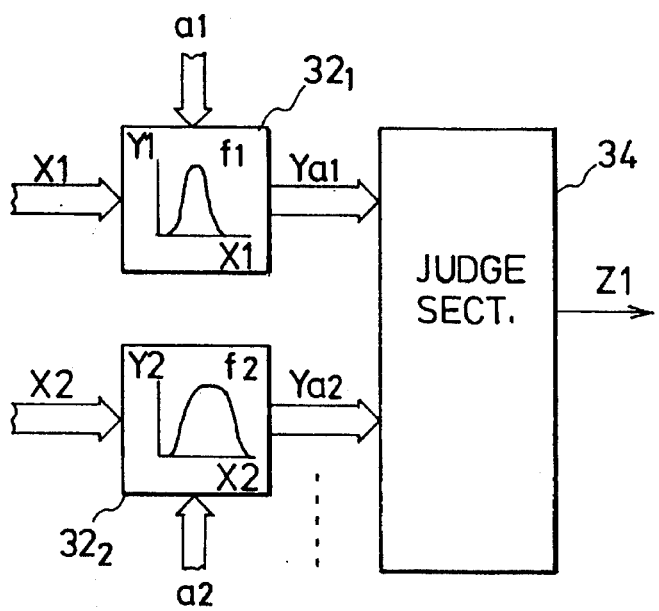
FIG. 2 is block diagram showing an overall configuration of a preferred embodiment of the particle judging device according to this invention.

Referring to FIG. 2, the particle judging device of this invention includes converting units $32_1$, $32_2$, . . . which receive detections signals X1, X2, . . . representing physical parameters of each particle, which are supplied from a particle detecting device (not shown) such as flow cytometer, and a judging unit 34 which receives the outputs of these converting units. The converting units $32_1$, $32_2$, . . . respectively store probability distribution functions $Y1=f_1(X1)$, $Y2=f_2(X2)$, . . . of detection signals representing the same physical parameters, which were obtained previously on a specific kind of particles. Therefore, these function values Y1, Y2, . . . represent the frequency of appearance of the detection signals when the detected signal belongs to the specific kind, that is, the probability of the detected particle belonging to the specific kind at the time of detection signals X1, X2, . . . , respectively. The input detection signals X1, X2, . . . are converted respectively into the values Y1, Y2, . . . representing the probabilities in accordance with the above-mentioned functions and, also, weighted respectively with separately provided weighting coefficients $a_1$, $a_2$, . . . in the converting units $32_1$, $32_2$, . . . , respectively, and the resultant weighted outputs $Ya_1(=a_1*Y1)$, $Ya_2(=a_2*Y2)$, . . . are supplied to the judging unit 34, as shown. The coefficients $a_1$, $a_2$, . . . are constants from zero to one, which are determined in accordance with the judging rule as described below. The judging unit 34 synthesizes the input signals $Ya_1$, $Ya_2$, . . . to calculate a value indicative of the synthesized probability and, also, compares it with a predetermined value to provide a judgement signal Z1. The processing in the converting units $32_1$, $32_2$, . . . and judging unit 34 are effected in real time fashion and, in fact, the time needed from reception of the detection signals X1, X2, . . . to delivery of the judgement signal is less than several hundred nanoseconds.

Figure 3:
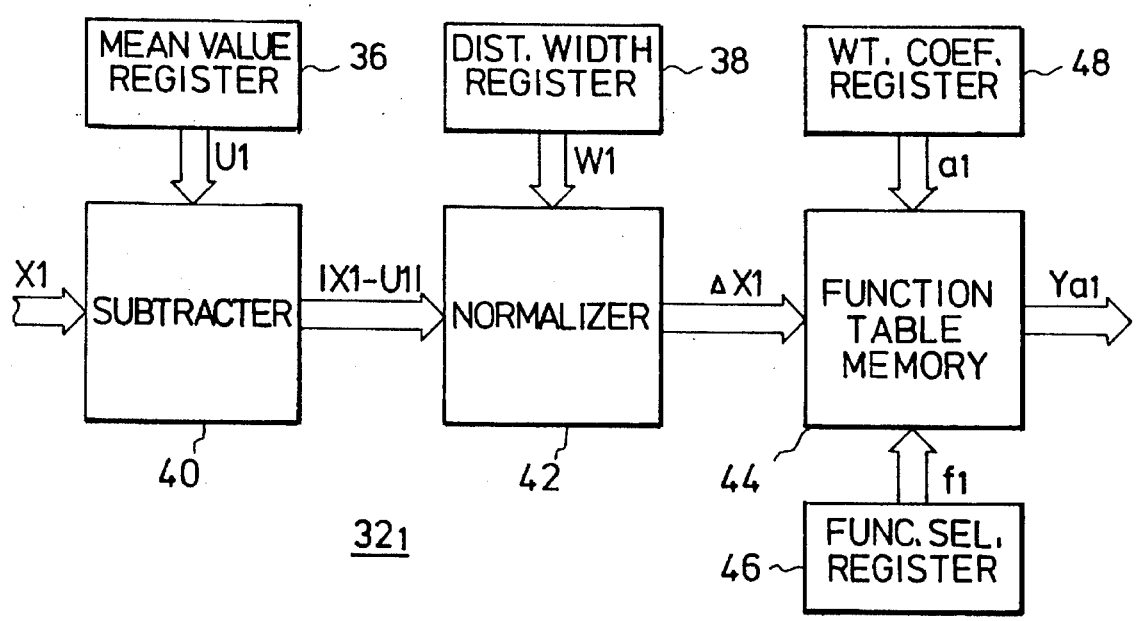
FIG. 3 is a block diagram showing a schematic configuration of a data converting unit in the embodiment of FIG. 2.

As shown in FIG. 3, the converting unit $32_1$ includes a mean value register 36 for storing a mean value U1 of the distribution expressed by the above function $f_1(X1)$, a distribution width register 38 for storing its distribution width W1 and a subtracter 40 and a normalizing unit 42 to which the contents of the registers 36 and 38 are supplied respectively. The distribution width may be selected as three times the standard deviation, for example. The subtracter 40 subtracts the mean value U1 from the input X1 to provide an absolute deviation |X1−U1|, and the normalizing unit 42 calculates a normalized deviation ΔX1 from the absolute deviation and the distribution width W1 in accordance with the following equation.

$$\Delta X1 = k_1(|X1-U1|/W1)$$

where $k_1$ is a constant.

Figure 4A:
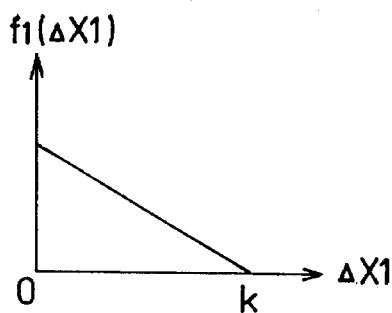
FIGS. 4a to 4d are diagrams showing examples of the function used in the data converting unit of FIG. 3.
Figure 4B:
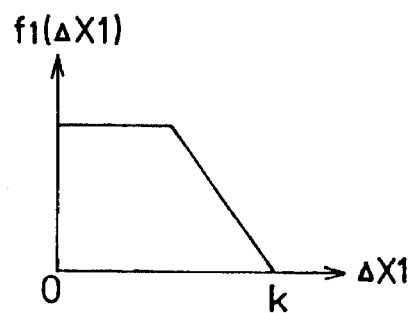
Figure 4C:
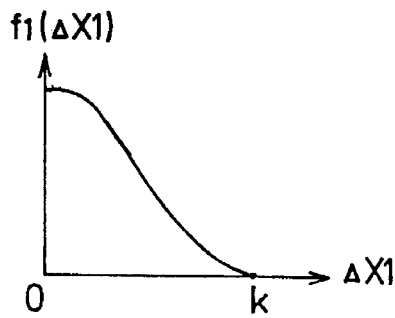
Figure 4D:
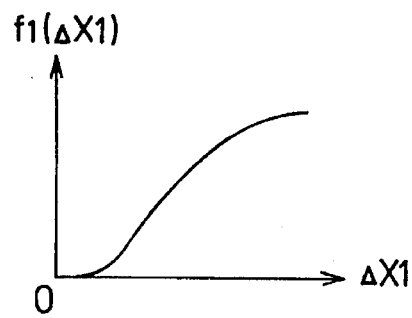

The normalized deviation ΔX1 is supplied to a function table memory 44 which is provided with a function select register 46 for selecting a function $f_1(\Delta X1)$. The function $f_1$ represents the relation between the normalized deviation ΔX1 and the probability of the corresponding detected particle being a particle of the specific kind, and it is determined on the basis of frequency distribution data of each physical parameter of the specific kind of particles. While this function is a decremental function whose value is maximum at zero value of the normalized deviation ΔX1 and becomes zero at a certain value k thereof, as shown in FIGS. 4a to 4c, it is possible to show the probability of the detected particle not being a particle of the specific kind with the value of the function if it is such an incremental function as shown in FIG. 4d. The normal distribution curve of FIG. 4c is suitable as the function $f_1$ since the frequency distribution curve of the physical parameter value is generally a normal distribution curve. However, such an approximate linear function as shown in FIG. 4a or 4b may be used for convenience in the function select register 46. One select code of such functions is preset by an external device (not shown) and supplied to the function table memory 44, in which its value $Y1=f_1(\Delta X1)$ is calculated.

The function table memory 44 is further provided with a weighting coefficient register 48 for storing various values off the weighting coefficient $a_1$. The value of the weighting coefficient $a_1$, which is specified in accordance with the undermentioned judging rule, is preset by an external device (not shown) and supplied to the function table memory 44. The table memory 44 calculates $Ya_1=a_1*Y1$ to deliver the probability output $Ya_1$.

It is recommendable to use a look-up table system for arithmetic operation of the units 40, 42 and 44 in order to raise their operation speed to effect, real time indication. Although the other converting units $32_2$, . . . of FIG. 2 may have the same circuit configuration as the above-mentioned converting unit $32_1$, it is necessary to select the probability functions $f_2$, . . . and weighting coefficients $a_2$, . . . so as to conform to the corresponding physical parameters, respectively.

Figure 5:
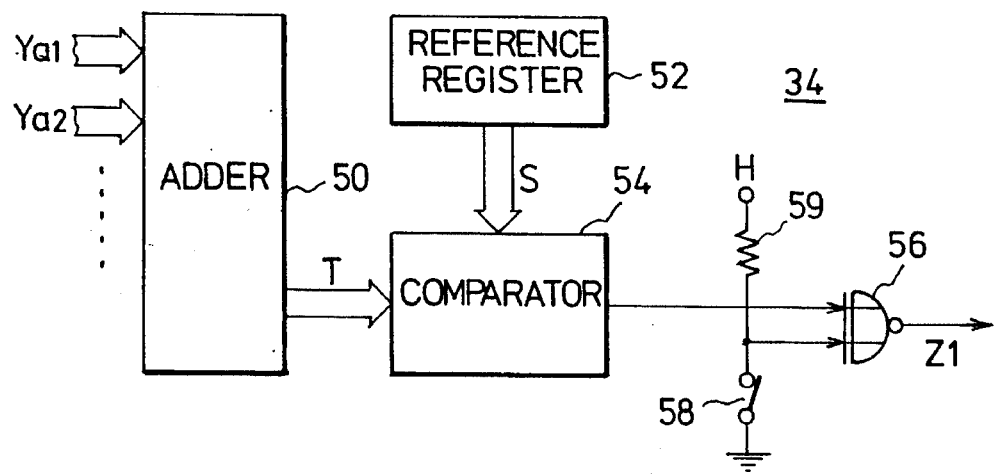
FIG. 5 is a block diagram showing a schematic configuration of the data converting unit in the embodiment of FIG.2.

Referring next to FIG. 5, the outputs $Ya_1$, $Ya_2$, . . . of the converting units $32_1$, $32_2$, . . . are supplied to an adder circuit 50 in the judging unit 34 and summed up and a resultant sum T ($=Ya_1+Ya_2+$ . . . ) is supplied as an object value of judgement to a comparator, which is provided with a reference register 52 for storing a reference value S for judgement, and compared with the reference value S. The comparator 54 is arranged to provide a "high" level output when the object value T is higher than the reference value S and its output terminal is connected to one of the input terminals of an exclusive-NOR circuit 56. The other input terminal of the exclusive-NOR circuit 56 is grounded through a switch 58 and also connected to a "high" level source terminal H through a resistor 59 so as to selectively receive a "high" or "low" level input. Therefore, the output Z1 of the exclusive-NOR circuit 56 shows affirmative decision at "low" level when the switch 58 is closed as shown, while it shows the same decision at "high" level when the switch 58 is open.

The above-mentioned judging process is executed in accordance with such a rule as described below in connection with some examples. In the following description, judgement is effected upon three characteristic parameters and detection signals X1, X2 and X3 respectively representing the values thereof are handled. For simplicity, however, the detection signals X1, X2 and X3 will be simply referred to as physical parameters X1, X2 and X3. Moreover, the particle which is caught by the particle detector and whose kind is to be identified will be referred to as "subject particle" and the particle of known kind, whose identity to the "subject particle" is to be judged, will be referred to as "object particle".

Rule-Example 1

A subject particle satisfying the following three conditions shall be judged as an object particle.

(1) Its physical parameter X1 is approximate to the mean value of the physical parameter X1 of the object particle, (2) its physical parameter X2 is approximate to the mean value of the physical parameter X2 of the object particle, and (3) its physical parameter X3 is approximate to the mean value of the physical parameter X3 of the object particle.

When the subject particle is an object particle, the judgement output Z1 of the exclusive NOR circuit 56 shall be at "low" level and the above-mentioned three conditions shall be equivalent in significance.

In order to realize the above-mentioned rule, the values of weighting coefficients $a_1$, $a_2$, and $a_3$ are made equal to unify the three conditions in significance, when the mean values, distribution widths, distribution functions and weighting coefficients of the physical parameters of the object particle are set respectively in the registers 36, 38, 46 and 48 of the converting units $32_1$, $32_2$ and $32_3$. The switch 58 of the judging unit is closed so that the output Z1 of the exclusive NOR circuit 56 is at "low" level in response to the "high" level output of the comparator 54. When there is such a relation as $T \geq S$ in this state between the sum T of the probability outputs $Ya_1$, $Ya_2$ and $Ya_3$ of the respective converting units $32_1$, $32_2$ and $32_3$ and the reference probability S, the output Z1 of the judging unit is at "low" level and the subject particle is judged as an object particle at probability T.

Rule-Example 2

A subject particle satisfying the following three conditions shall be judged as an object particle.

(1) Its physical parameter X1 is approximate to the mean value of the physical parameter X1 of the object particle, (2) its physical parameter X2 is approximate to the mean value of the physical parameter X2 of the object particle, and (3) its physical parameter X3 is approximate to the mean value of the physical parameter X3 of the object particle.

When the subject particle is an object particle, the judgement output Z1 of the exclusive NOR circuit 56 shall be at "low" level and the above-mentioned three conditions shall be high, medium and low in significance in this order.

In order to realize the above-mentioned rule, while the respective registers are set as same as in the case of Example 1, the weighting coefficients $a_1$, $a_2$ and $a_3$ are set in the weighting coefficient registers in the converting units $32_1$, $32_2$ and $32_3$ so as to make their mutual relation $a_1 > a_2 > a_3$. Moreover, the switch 58 of the judging unit is closed so that the output Z1 of the exclusive NOR circuit 56 is at "low" level in response to the "high" level output of the comparator 54. When the probability outputs of the converting units $32_1$, $32_2$ and $32_3$ are weighted differently as above, it is possible to effect more accurate judgement giving consideration to the significance of each condition. If the weighting coefficient is made zero, the corresponding physical parameter can be disregarded.

Figure 6:
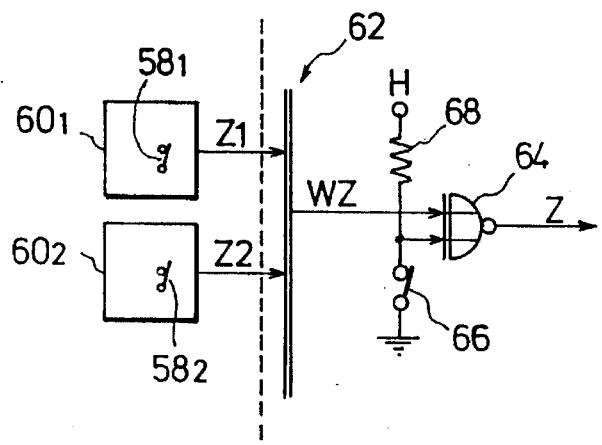
FIG. 6 is a block diagram showing a schematic configuration of a variation of the embodiment of FIG. 2.

It is also considered to apply plural rules differing in their contents as Examples 1 and 2 and provide synthesized affirmative decision in response to affirmative decision in accordance with any rule of them. In this case, as shown in FIG. 6, the outputs Z1, Z2, ... of particle judging blocks $60_1$, $60_2$, ... which execute their own rules respectively as above are connected in parallel by a wired OR line 62 and the output WZ of the wired OR line is connected to one input of an exclusive NOR circuit 64. As same as the exclusive NOR circuit 56, the other input of the exclusive NOR circuit 64 is grounded through a switch 66 and also connected through a resistor 68 to a "high" level source terminal H. The output WZ of the wired OR line 62 become "low" level if any one of the particle judging blocks $60_1$, $60_2$, ... (whose switches $58_1$, $58_2$, ... corresponding to the switch 58 are all closed) produces an affirmative output at "low" level. When the switch 66 is closed, therefore, the synthesized decision output Z of the exclusive NOR circuit 64 becomes "high" level if the condition based upon any judging rule is satisfied. When the switch 66 is open, the synthesized decision output Z becomes "high" level only when the outputs Z1, Z2, ... of all blocks $60_1$, $60_2$, ... are at "high" level, that is, when no condition based upon any rule is satisfied. Thus, it is possible to arbitrarily obtain affirmative or negative decision by controlling the switch 66.

The configuration of FIG. 6 has such an advantage in that the judging conditions can be easily changed, since the particle judging blocks $60_1$, $60_2$, ... storing various preset rules can be freely attached to and detached from the wired OR line.

Figure 7:
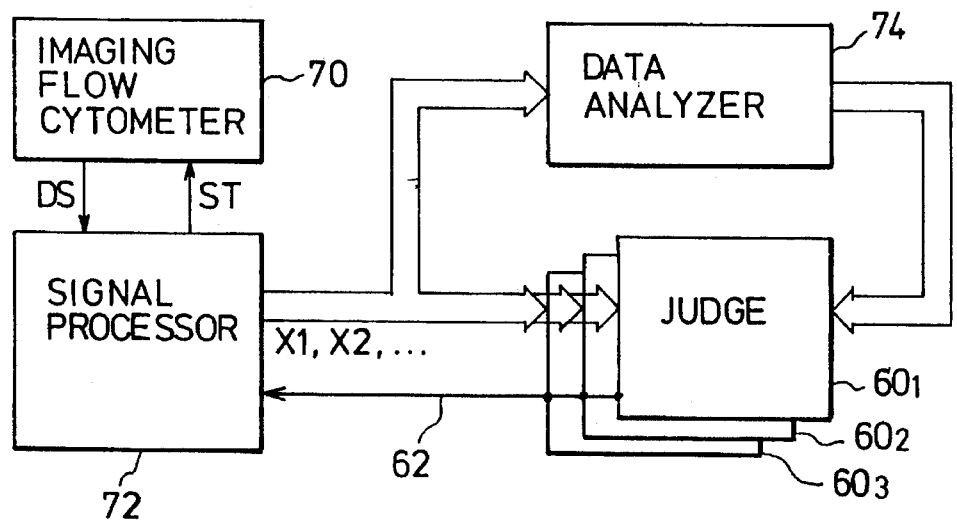
FIG 7 is a block diagram showing the embodiment of FIG. 2 co-operated with an imaging flow cytometer.

FIG. 7 shows a particle identifying system including particle judging blocks $60_1$, $60_2$, ... as described above combined with an imaging flow cytometer 70 as a particle detecting device. In this system, it is also possible to pick up and display a still image of each particle. The imaging flow cytometer 70 includes flow cell mechanism for forming a flat sheath flow of specimen, a light source and a light senser for detecting physical characteristics of each particle, a stroboscopic light source and a video camera for picking up the image of the particle, and the like. A detection signal DS of each particle obtained in the flow cytometer is supplied to a signal processing device 72 and converted here to respective parameter values X1, X2, ... in real time fashion. The physical parameter values X1, X2, ... are supplied respectively to particle judging blocks $60_1$, $60_2$, ... having various judging rules preset therein. The judging blocks return their decision outputs (Z1, Z2, ... ) through a wired OR line 62 to the signal processing device 72 within several hundred nanoseconds. The signal processing device 72 includes a circuit equivalent to the exclusive NOR circuit 64 and, when the subject particle is judged to be like an object particle, delivers a stroboscopic triggering signal ST to the flow cytometer 70. The stroboscopic light source of the flow cytometer flashes in response to the signal ST and the image of the subject particle is picked up by the video camera. The physical parameter values obtained from the signal processing device 72 are also supplied to a data analyzing device 74 and provided for statistical analysis using histograms and multidimensional scattergrams of the respective physical parameters. The result of analysis is supplied to the respective particle judging blocks $60_1$, $60_2$, ... for use in modification of the above-mentioned judging rules and preset conditions stored respectively therein.

The particle judging device of this invention can be combined with an imaging flow cytometer for picking up the image of a subject particle and, moreover, it may be combined with a sorting device such as a cell sorter for collecting the object particles only.

The above description of the embodiment is given only for the purpose of illustration and is not intended as any limitation of the invention. It should be obvious to those skilled in the art that various modificaton and changes can be.

I claim:

1. A particle judging device comprising:

means for detecting each particle from a specimen in which plural kinds of particles exist intermixedly and producing at least two detection signals each representing the value of one of at least two characteristic parameters of said particle;

means for storing mean values and distribution widths for each of said characteristic parameters representative of various specific kinds of particle;

means for calculating respective deviations of each of said detection signals from a corresponding one of said mean values;

means for normalizing each respective deviation based upon a corresponding one of said distribution widths to obtain respective normalized deviations;

means for storing respective predetermined probability distribution functions;

means for determining respective probabilities for each of said respective normalized deviations based upon a corresponding one of said probability distribution functions;

means for weighting each of said respective probabilities of said normalized deviations in accordance with a predetermined rule to produce weighted probabilities; and judging means for judging whether said particle belongs to any one of said specific kinds or not, on the basis of said weighted probabilities.

2. The particle judging device as set forth in claim 1, wherein said means for storing respective predetermined probability distribution functions comprises means for storing plural functions and selecting and supplying one of said plural functions to said probability determining means.

3. The particle judging device as set forth in claim 1, and further comprising:

switch means for selectively inverting a logic of an output of said judging means.

4. The particle judging device as set forth in claim 1, and further comprising:

a plurality of said judging means for judging whether said particle belongs to any one of said specific kinds or not, corresponding to a plurality of particle judging rules, and wired OR means for receiving results of judgment of said plurality of judging means and for delivering a judgment signal at an output of said wired OR means.

5. The particle judging device as set forth in claim 1, further comprising means for generating, in response to a determination by said judging means that said particle belongs to said one specific kind, a strobe triggering signal for driving a stroboscopic light source to capture an image of said particle.

6. A particle judging device for comparing a candidate particle with an object particle of a known type, comprising:

means for receiving a plurality of detection signals each corresponding to a different type of physical measurement obtained from said candidate particle;

means for storing, for each of said plurality of detection signals, a probability distribution function which correlates values of the detection signal with a probability that said candidate particle matches said object particle;

means for converting each said detection signal into one of said probabilities by applying said probability distribution function to a respective detection signal;

means for weighting each of said probabilities output by said converting means by applying a coefficient determined in accordance with a predetermined judging rule;

an adder for adding each of said weighted probabilities into a summed value; and a comparator, coupled to said adder and to a reference value register, for comparing said summed value with a reference value stored in said reference value register and outputting a judgment signal indicative of a match, wherein said converting means comprises means for determining a deviation from a stored mean value for each of said detection signals; and means for normalizing each of said determined deviations in accordance with a stored distribution width.

* * * * *